(12) United States Patent
Schwartz et al.

(10) Patent No.: US 9,439,991 B2
(45) Date of Patent: Sep. 13, 2016

(54) CONTAINER AND SYSTEM FOR DECONTAMINATING A MEDICAL DEVICE WITH A FLUID

(71) Applicant: Medivators, Inc., Minneapolis, MN (US)

(72) Inventors: Mason Schwartz, Elk River, MN (US); Jonathan K. Olson, Delano, MN (US); Thomas M. Gentle, Jr., St. Michael, MN (US); John E. Marxer, Eagan, MN (US); Michael P. Petersen, Eden Prairie, MN (US)

(73) Assignee: MEDIVATORS INC., Minneapolis, MN (US)

( * ) Notice: Subject to any disclaimer, the term of this patent is extended or adjusted under 35 U.S.C. 154(b) by 0 days.

(21) Appl. No.: 14/473,368

(22) Filed: Aug. 29, 2014

(65) Prior Publication Data

US 2014/0369887 A1 Dec. 18, 2014

Related U.S. Application Data

(62) Division of application No. 12/959,535, filed on Dec. 3, 2010, now Pat. No. 8,821,807.

(60) Provisional application No. 61/266,309, filed on Dec. 3, 2009.

(51) Int. Cl.
*A61L 2/00* (2006.01)
*A61L 2/20* (2006.01)
(Continued)

(52) U.S. Cl.
CPC ............... *A61L 2/20* (2013.01); *A61B 50/30* (2016.02); *A61L 2/22* (2013.01); *A61L 2/24* (2013.01); *A61L 2/26* (2013.01); *A61B 2050/314* (2016.02); *A61L 2202/24* (2013.01)

(58) Field of Classification Search
CPC .......................................................... A61L 2/20
USPC .......................................................... 422/292
See application file for complete search history.

(56) References Cited

U.S. PATENT DOCUMENTS

| 1,062,404 A | 5/1913 | Kiefer |
| 1,114,880 A | 10/1914 | Hall |

(Continued)

FOREIGN PATENT DOCUMENTS

| CN | 1141003 A | 1/1997 |
| CN | 1585817 A | 2/2005 |

(Continued)

OTHER PUBLICATIONS

"Cantel Subsidiary Receives Expanded EPO Approval for Minncare Cold Sterilant in Fogging Applications", Business Wire, Jul. 4, 2008, 1 page.

(Continued)

*Primary Examiner* — Kevin Joyner
(74) *Attorney, Agent, or Firm* — Faegre Baker Daniels LLP

(57) ABSTRACT

A method for decontaminating a medical device includes enclosing the medical device in an enclosure including a fog-permeable layer and an exterior port member coupled to the fog-permeable layer. The exterior port member of the enclosure is coupled to a chemical dispersing interface in a decontamination chamber. A pressure in the decontamination chamber is reduced to a sub-atmospheric pressure in a first evacuation step. A room temperature decontaminating fluid is introduced as a fog into the decontamination chamber. The fog is held in the decontamination chamber for a decontaminating time. The pressure in the decontamination chamber is reduced to a sub-atmospheric pressure in a second evacuation step. The decontamination chamber is vented to atmospheric pressure.

10 Claims, 6 Drawing Sheets

(51) Int. Cl.
*A61L 2/22* (2006.01)
*A61L 2/26* (2006.01)
*A61L 2/24* (2006.01)

(56) References Cited

U.S. PATENT DOCUMENTS

| | | |
|---|---|---|
| 1,837,264 A | 12/1931 | Hackley |
| 2,965,936 A | 6/1957 | Kaye |
| 2,836,570 A | 5/1958 | Peers |
| 3,114,599 A | 12/1963 | Fanning |
| 3,436,173 A | 4/1969 | Power |
| 3,498,742 A | 3/1970 | Long |
| 3,547,576 A | 12/1970 | Sheikh |
| 3,816,074 A | 6/1974 | Decupper |
| 3,936,270 A | 2/1976 | Gunther |
| 3,958,935 A | 5/1976 | Kowol |
| 4,064,062 A | 12/1977 | Yurko |
| 4,119,400 A | 10/1978 | Kurz |
| 4,169,123 A | 9/1979 | Moore et al. |
| 4,169,124 A | 9/1979 | Forstrom et al. |
| 4,230,663 A | 10/1980 | Forstrom et al. |
| 4,241,010 A | 12/1980 | Baran |
| 4,241,020 A | 12/1980 | Grantham |
| 4,249,265 A | 2/1981 | Coester |
| 4,259,103 A | 3/1981 | Malek et al. |
| 4,270,658 A | 6/1981 | Schuster |
| 4,294,804 A | 10/1981 | Baran |
| 4,366,125 A | 12/1982 | Kodera et al. |
| 4,447,399 A | 5/1984 | Runnells et al. |
| 4,457,892 A | 7/1984 | Young |
| 4,483,771 A | 11/1984 | Koch |
| 4,512,951 A | 4/1985 | Koubek |
| 4,587,264 A | 5/1986 | Jourdan-Laforte et al. |
| 4,592,896 A | 6/1986 | Runnells et al. |
| 4,637,916 A | 1/1987 | Hennebert et al. |
| 4,643,876 A | 2/1987 | Jacobs et al. |
| 4,687,635 A | 8/1987 | Kaehler et al. |
| 4,744,951 A | 5/1988 | Cummings et al. |
| 4,756,882 A | 7/1988 | Jacobs et al. |
| 4,843,867 A | 7/1989 | Cummings |
| 4,892,705 A | 1/1990 | Sternfeld et al. |
| 4,904,901 A | 2/1990 | Simopoulos et al. |
| 4,921,675 A | 5/1990 | Johnson |
| 4,943,414 A | 7/1990 | Jacobs et al. |
| 4,952,370 A | 8/1990 | Cummings et al. |
| 4,956,145 A | 9/1990 | Cummings et al. |
| 4,986,963 A | 1/1991 | Corcoran et al. |
| 5,008,079 A | 4/1991 | Wltzler et al. |
| 5,258,162 A | 11/1993 | Andersson et al. |
| 5,340,878 A | 8/1994 | Sadatoshi et al. |
| 5,460,962 A | 10/1995 | Kemp |
| 5,482,683 A | 1/1996 | Sheth et al. |
| 5,508,009 A | 4/1996 | Rickloff et al. |
| 5,512,244 A | 4/1996 | Griffiths et al. |
| 5,527,508 A | 6/1996 | Childers et al. |
| 5,534,221 A | 7/1996 | Hillebrenner et al. |
| 5,556,607 A | 9/1996 | Childers et al. |
| 5,580,530 A | 12/1996 | Kowatsch et al. |
| 5,620,656 A | 4/1997 | Wensky et al. |
| 5,641,455 A | 6/1997 | Rosenlund et al. |
| 5,667,753 A | 9/1997 | Jacobs et al. |
| 5,674,450 A | 10/1997 | Lin et al. |
| 5,676,837 A | 10/1997 | Jungbauer et al. |
| 5,733,503 A | 3/1998 | Kowatsch et al. |
| 5,741,460 A | 4/1998 | Jacob et al. |
| 5,779,973 A | 7/1998 | Edwards et al. |
| 5,784,934 A | 7/1998 | Izumisawa |
| 5,792,422 A | 8/1998 | Lin et al. |
| 5,801,010 A | 9/1998 | Falkowski et al. |
| 5,834,313 A | 11/1998 | Lin |
| 5,847,393 A | 12/1998 | Van Den Berg et al. |
| 5,851,483 A | 12/1998 | Nicolle et al. |
| 5,863,499 A | 1/1999 | Kralovic |
| 5,869,000 A | 2/1999 | DeCato |
| 5,876,666 A | 3/1999 | Lin et al. |
| D408,837 S | 4/1999 | Gotham et al. |
| 5,902,413 A | 5/1999 | Puszko et al. |
| 5,904,901 A | 5/1999 | Shimono et al. |
| 5,906,794 A | 5/1999 | Childers |
| 5,955,025 A | 9/1999 | Barrett |
| 5,961,921 A | 10/1999 | Addy et al. |
| 5,980,825 A | 11/1999 | Addy et al. |
| 6,010,662 A | 1/2000 | Lin et al. |
| 6,030,579 A | 2/2000 | Addy et al. |
| 6,036,918 A | 3/2000 | Kowanko |
| 6,039,922 A | 3/2000 | Swank et al. |
| 6,041,794 A | 3/2000 | Lin et al. |
| 6,066,294 A | 5/2000 | Lin et al. |
| 6,094,887 A | 8/2000 | Swank et al. |
| 6,096,265 A | 8/2000 | Mezger et al. |
| 6,096,266 A | 8/2000 | Duroselle |
| 6,120,730 A | 9/2000 | Swank et al. |
| 6,135,433 A | 10/2000 | Nurmi |
| 6,162,394 A | 12/2000 | Nicolle et al. |
| 6,162,395 A | 12/2000 | Kowanko |
| 6,183,691 B1 | 2/2001 | Swank et al. |
| D438,980 S | 3/2001 | Hehenberger |
| 6,234,310 B1 | 5/2001 | Goldhaber |
| 6,269,680 B1 | 8/2001 | Prieve et al. |
| 6,286,527 B1 | 9/2001 | Stanley |
| 6,312,645 B1 | 11/2001 | Lin et al. |
| 6,312,646 B2 | 11/2001 | Kowanko |
| 6,354,312 B1 | 3/2002 | Lin et al. |
| 6,365,102 B1 | 4/2002 | Wu et al. |
| 6,365,103 B1 | 4/2002 | Fournier |
| 6,391,260 B1 | 5/2002 | Davis et al. |
| 6,406,666 B1 | 6/2002 | Cicha et al. |
| 6,439,246 B2 | 8/2002 | Stanley |
| 6,451,254 B1 | 9/2002 | Wang et al. |
| 6,468,472 B1 | 10/2002 | Yu et al. |
| 6,495,100 B1 | 12/2002 | Lin et al. |
| 6,528,017 B2 | 3/2003 | Jacobs et al. |
| 6,530,399 B2 | 3/2003 | Nguyen et al. |
| 6,582,654 B1 | 6/2003 | Kral et al. |
| 6,594,971 B1 | 7/2003 | Addy et al. |
| 6,596,231 B1 | 7/2003 | Catelli et al. |
| 6,600,444 B2 | 7/2003 | Desjardins |
| 6,641,781 B2 | 11/2003 | Walta |
| 6,673,313 B2 | 1/2004 | Wang et al. |
| 6,746,647 B2 | 6/2004 | Kohler et al. |
| 6,790,410 B2 | 9/2004 | Metzner et al. |
| 6,797,234 B2 | 9/2004 | Stanley |
| 6,884,392 B2 | 4/2005 | Malkin et al. |
| 6,977,061 B2 | 12/2005 | Lin et al. |
| 6,998,582 B1 | 2/2006 | Maroti |
| 7,001,873 B2 | 2/2006 | McDonnell et al. |
| 7,005,549 B2 | 2/2006 | Hobson et al. |
| 7,025,932 B2 | 4/2006 | Martin et al. |
| 7,146,746 B2 | 12/2006 | Kawasaki |
| 7,178,555 B2 | 2/2007 | Engle et al. |
| 7,179,419 B2 | 2/2007 | Lin et al. |
| 7,186,371 B1 | 3/2007 | Watling |
| 7,186,372 B2 | 3/2007 | Kohler et al. |
| 7,186,374 B2 | 3/2007 | Zelina et al. |
| 7,294,305 B2 | 11/2007 | Lin et al. |
| 7,303,073 B2 | 12/2007 | Raynal-Olive et al. |
| 7,307,191 B2 | 12/2007 | Hobson et al. |
| 7,326,382 B2 | 2/2008 | Adiga et al. |
| 7,434,372 B2 | 10/2008 | Vanhamel et al. |
| 7,449,145 B2 | 11/2008 | Kohler et al. |
| 7,452,504 B2 | 11/2008 | Wu et al. |
| 7,468,159 B2 | 12/2008 | Lin et al. |
| 7,491,371 B2 | 2/2009 | Moller et al. |
| 7,541,002 B2 | 6/2009 | Centanni |
| 7,556,767 B2 | 7/2009 | Lin et al. |
| 7,569,180 B2 | 8/2009 | Kohler et al. |
| 7,578,969 B2 | 8/2009 | Mielnik et al. |
| 7,604,773 B2 | 10/2009 | Ekstrom et al. |
| 7,608,218 B2 | 10/2009 | Fryer et al. |
| 7,611,667 B2 | 11/2009 | Centanni |
| 7,615,187 B2 | 11/2009 | Helton et al. |
| 7,622,074 B2 | 11/2009 | Mielnik |
| 7,651,667 B2 | 1/2010 | McVey et al. |
| 7,670,550 B2 | 3/2010 | Lin et al. |

(56) References Cited

U.S. PATENT DOCUMENTS

| | | | |
|---|---|---|---|
| 7,670,565 B2 | 3/2010 | McVey et al. |
| 7,678,339 B2 | 3/2010 | Wira |
| 7,713,473 B2 | 5/2010 | Kendall et al. |
| 7,718,122 B2 | 5/2010 | Smith et al. |
| 7,803,315 B2 | 9/2010 | McDonnell et al. |
| 7,807,100 B2 | 10/2010 | Choperena et al. |
| 7,811,531 B2 | 10/2010 | Mielnik et al. |
| 7,850,925 B2 | 12/2010 | Centanni et al. |
| 7,988,911 B2 | 8/2011 | Centanni et al. |
| 7,988,920 B2 | 8/2011 | Centanni et al. |
| 7,993,602 B2 | 8/2011 | Moriyama et al. |
| 8,012,424 B2 | 9/2011 | Jethrow et al. |
| 8,025,848 B2 | 9/2011 | McVey et al. |
| 8,056,719 B2 | 11/2011 | Porret et al. |
| 8,062,590 B1 | 11/2011 | Ricciardi et al. |
| 8,110,156 B2 | 2/2012 | Ricciardi et al. |
| 8,128,789 B2 | 3/2012 | Hirata et al. |
| 8,133,437 B2 | 3/2012 | Scalzo et al. |
| 8,178,357 B2 | 5/2012 | Trogler et al. |
| 8,236,240 B2 | 8/2012 | Childers et al. |
| 8,298,482 B2 | 10/2012 | Rees et al. |
| 8,343,422 B2 | 1/2013 | Sato et al. |
| 8,343,437 B2 | 1/2013 | Patel |
| 8,357,331 B2 | 1/2013 | McVey et al. |
| 8,425,837 B2 | 4/2013 | Carbone et al. |
| 8,444,919 B2 | 5/2013 | Erickson |
| 8,821,807 B2 | 9/2014 | Schwartz et al. |
| 8,889,081 B2 | 11/2014 | Schwartz et al. |
| 9,017,607 B2 | 4/2015 | Olson et al. |
| 2001/0000227 A1 | 4/2001 | Kowanko |
| 2001/0036422 A1 | 11/2001 | Lin et al. |
| 2001/0053333 A1 | 12/2001 | Messier et al. |
| 2002/0069616 A1 | 6/2002 | Odell et al. |
| 2002/0081228 A1 | 6/2002 | Hui et al. |
| 2002/0085950 A1 | 7/2002 | Robitaille et al. |
| 2002/0114727 A1 | 8/2002 | McVey et al. |
| 2002/0122744 A1 | 9/2002 | Hui et al. |
| 2002/0168289 A1 | 11/2002 | McVey |
| 2002/0187067 A1 | 12/2002 | Lukasik et al. |
| 2003/0017074 A1 | 1/2003 | Wang et al. |
| 2003/0086820 A1 | 5/2003 | McDonnell et al. |
| 2003/0124026 A1 | 7/2003 | Williams et al. |
| 2003/0133834 A1 | 7/2003 | Karle |
| 2003/0138347 A1 | 7/2003 | Lin |
| 2003/0190253 A1 | 10/2003 | Kohler et al. |
| 2003/0235511 A1 | 12/2003 | Jacobs et al. |
| 2004/0001776 A1 | 1/2004 | Fryer et al. |
| 2004/0005240 A1 | 1/2004 | Adiga et al. |
| 2004/0005259 A1 | 1/2004 | Sacca |
| 2004/0022671 A1 | 2/2004 | Malatesta |
| 2004/0022673 A1 | 2/2004 | Protic |
| 2004/0028556 A1 | 2/2004 | Frost et al. |
| 2004/0052679 A1 | 3/2004 | Root et al. |
| 2004/0081601 A1 | 4/2004 | Morrissey et al. |
| 2004/0162228 A1 | 8/2004 | Hobson et al. |
| 2004/0170527 A1 | 9/2004 | Jacobs et al. |
| 2004/0184950 A1 | 9/2004 | McVey et al. |
| 2005/0013726 A1 | 1/2005 | Hill et al. |
| 2005/0042130 A1 | 2/2005 | Lin et al. |
| 2005/0084431 A1 | 4/2005 | Hill et al. |
| 2005/0147527 A1 | 7/2005 | Brown et al. |
| 2005/0196313 A1 | 9/2005 | Choperena et al. |
| 2005/0252274 A1 | 11/2005 | Centanni |
| 2005/0260097 A1 | 11/2005 | Williams et al. |
| 2006/0078459 A1 | 4/2006 | Kohler et al. |
| 2006/0088441 A1 | 4/2006 | Hill |
| 2006/0099106 A1 | 5/2006 | Watling et al. |
| 2007/0003431 A1 | 1/2007 | Kendall et al. |
| 2007/0014691 A1 | 1/2007 | Jacobs et al. |
| 2007/0034095 A1 | 2/2007 | McDonnell et al. |
| 2007/0053813 A1 | 3/2007 | Martin |
| 2007/0092398 A1 | 4/2007 | McDonald |
| 2007/0098592 A1 | 5/2007 | Buczynski et al. |
| 2007/0160491 A1 | 7/2007 | Kohler et al. |
| 2007/0207054 A1 | 9/2007 | Langford |
| 2007/0253859 A1 | 11/2007 | Hill |
| 2008/0240981 A1 | 10/2008 | Berentsveig et al. |
| 2009/0209031 A1 | 8/2009 | Stopek |
| 2009/0324445 A1 | 12/2009 | Kohler et al. |
| 2010/0011823 A1 | 1/2010 | Dahms et al. |
| 2010/0028200 A1 | 2/2010 | Shiosawa |
| 2010/0034697 A1 | 2/2010 | Weinberger et al. |
| 2010/0034707 A1 | 2/2010 | Mielnik et al. |
| 2010/0143218 A1 | 6/2010 | Nurminen et al. |
| 2010/0196197 A1 | 8/2010 | Rovison, Jr. et al. |
| 2010/0226821 A1 | 9/2010 | Ricciardi et al. |
| 2010/0296969 A1 | 11/2010 | Ngo et al. |
| 2010/0297776 A1 | 11/2010 | Trogler et al. |
| 2010/0303671 A1 | 12/2010 | Bertrand |
| 2010/0316527 A1 | 12/2010 | McLaren et al. |
| 2011/0044851 A1 | 2/2011 | Centanni et al. |
| 2011/0044852 A1 | 2/2011 | Ryan et al. |
| 2011/0052449 A1 | 3/2011 | Centanni et al. |
| 2011/0076189 A1 | 3/2011 | McVey et al. |
| 2011/0076192 A1 | 3/2011 | Robitaille et al. |
| 2011/0079525 A1 | 4/2011 | Peck et al. |
| 2011/0091354 A1 | 4/2011 | Schwartz et al. |
| 2011/0135537 A1 | 6/2011 | Schwartz et al. |
| 2011/0165299 A1 | 7/2011 | Sato et al. |
| 2011/0182772 A1 | 7/2011 | Holt |
| 2012/0009085 A1 | 1/2012 | Burger |
| 2012/0189494 A1 | 7/2012 | Rovison, Jr. et al. |
| 2012/0219456 A1 | 8/2012 | Childers et al. |
| 2012/0277662 A1 | 11/2012 | Golkowski |
| 2012/0301356 A1 | 11/2012 | Olson et al. |
| 2013/0065958 A1 | 3/2013 | Dunn |
| 2013/0101462 A1 | 4/2013 | Keil |
| 2015/0064066 A1 | 3/2015 | Schwartz et al. |
| 2015/0202339 A1 | 7/2015 | Schwartz et al. |

FOREIGN PATENT DOCUMENTS

| | | |
|---|---|---|
| CN | 102018966 B | 4/2011 |
| CN | 103702689 A | 4/2014 |
| EP | 0302420 A2 | 2/1989 |
| EP | 0774263 A1 | 5/1997 |
| EP | 0923951 B1 | 6/1999 |
| EP | 1378253 A1 | 1/2004 |
| EP | 1481692 B1 | 12/2004 |
| EP | 1813220 A1 | 8/2007 |
| EP | 1473044 B1 | 12/2007 |
| EP | 1171368 B1 | 2/2008 |
| EP | 1935515 A2 | 6/2008 |
| EP | 1308173 B1 | 12/2008 |
| EP | 1110557 B1 | 3/2009 |
| EP | 2228076 A1 | 9/2010 |
| EP | 2714101 A1 | 4/2014 |
| EP | 2506884 B1 | 2/2015 |
| JP | 08126605 A | 5/1996 |
| JP | 11015570 A | 1/1999 |
| JP | 11137650 A | 5/1999 |
| JP | 2002508219 A | 3/2002 |
| JP | 2003260118 A | 9/2003 |
| JP | 2005143669 A | 6/2005 |
| JP | 2007167546 A | 7/2007 |
| JP | 2009513213 A | 4/2009 |
| JP | 2009131296 A | 6/2009 |
| JP | 2009268466 A | 11/2009 |
| WO | WO0207788 A1 | 1/2002 |
| WO | WO0249682 A1 | 6/2002 |
| WO | 2006013089 A1 | 2/2006 |
| WO | WO2007008205 A1 | 1/2007 |
| WO | WO2007049076 A1 | 5/2007 |
| WO | WO2008014615 A1 | 2/2008 |
| WO | WO2012128734 A1 | 9/2012 |
| WO | 2012173756 A1 | 12/2012 |

OTHER PUBLICATIONS

European Search Report issued in EP Application No. 13152441, mailed Feb. 27, 2013, 8 pages.

FMC Material Safety Data Sheet, Date Approved Nov. 10, 2006, 11 pages.

(56) References Cited

OTHER PUBLICATIONS

International Search Report and Written Opinion issued in PCT/US2010/052622, mailed Jan. 20, 2011, 14 pages.

International Search Report and Written Opinion issued in PCT/US2010/058885, mailed Feb. 10, 2011, 11 pages.

International Search Report and Written Opinion issued in PCT/US2012/039160, mailed Oct. 2, 2012.

International Standard, ISO 11140-1, 2nd Edition Jul. 15, 2005, Sterilization of Health Care Products—Chemical Indicators—Part 1: General Requirements, pp. 1-27.

Lunger, MJ et al., "Reducing Pump-Down Time With Dry Air Venting", 43rd Annual Technical Conference Proceedings, Denver, Apr. 15-20, 2000, 1 page.

Minncare Dry Fog™ System: An Integral part of Modern Cleanroom Disinfection Procedures, © 2009 Mar Cor Purification, 4 pages.

Portner, Dorothy M. et al., "Sporicidal Effect of Peracetic Acid Vapor", Applied Microbiology, vol. 16, No. 11, Nov. 1968, pp. 1782-1785.

Rutala, William A. et al., "New Disinfection and Sterilization Methods", Emerging Infectious Diseases Journal, vol. 7, No. 2, Mar.-Apr. 2001, 14 pages.

The Mini Fog System: A Modern Method to Enhance Small Space Disinfection, © 2008 Mar Cor Purification, 2 pages.

"Vapor Liquid-/Solid System", Retrieved from Internet electronic mail: http://blowers.chee.arizona.edu/201project/Glsys.interrelatn.pgl.HTML/, retrieved on Dec. 10, 2014, Vapor-Liquid/Solid Equilibruim, (C) 2007, 8 pages.

International Preliminary Report on Patentability issued in PCT/US2012/039160, mailed Dec. 12, 2013, 7 pages.

CONTAINER AND SYSTEM FOR DECONTAMINATING A MEDICAL DEVICE WITH A FLUID

CROSS-REFERENCE TO RELATED APPLICATION

This application is a divisional of U.S. application Ser. No. 12/959,535, filed Dec. 3, 2010, now U.S. Pat. No. 8,821,807, which claims the benefit of Provisional Application No. 61/266,309, filed Dec. 3, 2009, both of which are incorporated herein by reference in their entirety.

TECHNICAL FIELD

The present invention relates to decontamination of medical devices. More particularly, the present invention relates to containers and systems for decontaminating a medical device with a fluid.

BACKGROUND

Robust medical equipment is often sterilized at high temperatures. Commonly, the equipment is sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Further, endoscopes in particular present problems in that such devices typically have numerous exterior crevices and interior lumens which can harbor microbes. The employment of a fast-acting yet gentler sterilization method is desirable for reprocessing sensitive instruments such as endoscopes. Other medical or dental instruments which comprise lumens, crevices, and the like are also in need of methods of cleaning and decontaminating which employ an effective reprocessing system which will minimize harm to sensitive components and materials.

SUMMARY

The present invention relates to a method for decontaminating a medical device. The medical device is enclosed in an enclosure including a fog-permeable layer and an exterior port member coupled to the fog-permeable layer. The exterior port member of the enclosure is coupled to a chemical dispersing interface in a decontamination chamber. A pressure in the decontamination chamber is reduced to a sub-atmospheric pressure in a first evacuation step. A room temperature decontaminating fluid is introduced as a fog into the decontamination chamber. The fog is held in the decontamination chamber for a decontaminating time. The pressure in the decontamination chamber is reduced to a sub-atmospheric pressure in a second evacuation step. The decontamination chamber is vented to atmospheric pressure.

While multiple embodiments are disclosed, still other embodiments of the present invention will become apparent to those skilled in the art from the following detailed description, which shows and describes illustrative embodiments of the invention as well as other combinations or permutations of aspects of these various embodiments. Accordingly, the drawings and detailed description are to be regarded as illustrative in nature and not restrictive.

Figure 1:
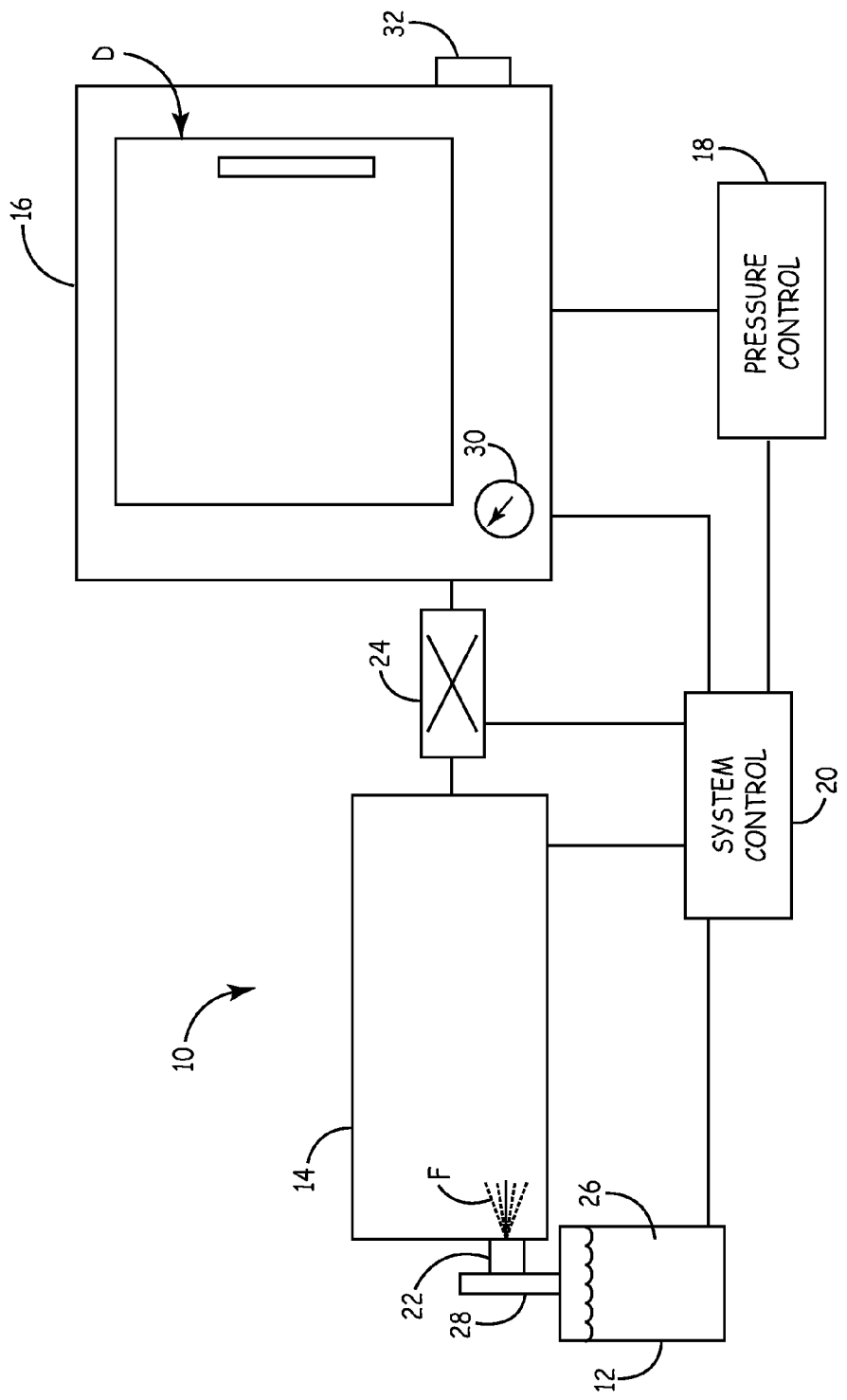
FIG. 1 is a schematic view of a system for decontaminating a medical device, according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for decontaminating a medical, dental, or other device according to an embodiment of the present invention. The system includes a reservoir 12, a chemical or fog chamber 14, a decontamination chamber 16, a pressure control assembly 18, and a system controller 20. The reservoir 12 is in fluid communication with the chemical chamber 14 via a nozzle 22. The chemical chamber 14 is in fluid communication with the decontamination chamber 16 via a fluid control valve 24. The system controller 20 provides control signals to and/or receives control signals from the reservoir 12, chemical chamber 14, decontamination chamber 16, pressure control assembly 18, and fluid control valve 24. In some embodiments, the system 10 is assembled in a device small enough to sit on a tabletop or counter. For example, the decontamination chamber 16 may have an interior volume of less than about ten cubic feet. The medical device to be decontaminated is placed into the decontamination chamber 16 by opening the door D and placing the medical device on a rack or other supporting assembly in the interior of the decontamination chamber 16.

The chemical reservoir 12 may be a holding tank or other assembly configured to hold a decontaminating substance 26. In some embodiments, the decontaminating substance 26 is a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, Va.: AAMI 2005). In some embodiments, the decontaminating substance 26 is a room temperature (e.g, 20° C. to 25° C.) substance that can be dispersed as a fog during the decontamination process. For example, the decontaminating substance 26 may include hydrogen peroxide ($H_2O_2$) and/or peracetic acid (PAA).

The system controller 20 controls delivery of the decontaminating substance 26 from the reservoir 12 to the nozzle 22. The decontaminating substance 26 may be pushed or pulled through a tube 28 that connects the reservoir 12 to the nozzle 22. In some embodiments, the nozzle 22 is an atomizing nozzle that is configured to transform the decontaminating substance 26 at the input of the nozzle 22 to a fog F at the output of the nozzle 22. To produce the fog F, the atomizing nozzle may generate fine droplets of the decontaminating substance 26 that average, for example, less than about 10 μm. Droplets of this size tend to bounce off of solid surfaces, allowing for even dispersion, while avoiding excessive condensation, corrosion, and surface wetting issues in the chemical chamber 14. In addition, the small droplets evaporate, and the vapor penetrates normally inaccessible areas, resulting in a more effective process. One example nozzle 22 that may be suitable for use in the system 10 is a nozzle such as that used in the Minncare Dry Fog® or Mini Dry Fog systems, sold by Mar Cor Purification, Skippack, Pa. Another example nozzle 22 that may be suitable for use in the system 10 is a spray nozzle assembly including Spraying Systems Co. product numbers 1/4J-316SS, SU1A-316SS, and 46138-16-316SS, sold by Spraying Systems Co., Wheaton, Ill.

The fog F is dispersed into the interior of the chemical chamber 14. The amount of fog F generated in the chemical chamber 14 is controlled by the system controller 20 by controlling the rate and amount of the decontaminating substance 26 that is forced through the nozzle 22. The rate and amount of decontaminating substance 26 that is forced through the nozzle 22 may be preprogrammed into the system controller 20 or may be manually entered into the system controller 20 by a user of the system 10. In addition, the system controller 20 may include multiple programs that provide different rates and amounts of the decontaminating substance 26 to the nozzle 22.

When the desired or programmed amount of fog F has been dispersed into the chemical chamber 14, the fog F is transferred into the decontamination chamber 16. In some embodiments, the system controller 20 commands the pressure controller 18 to develop a pressure differential between the chemical chamber 14 and the decontamination chamber 16. For example, the pressure controller 18 may evacuate the decontamination chamber 16 to produce a vacuum or partial vacuum in the decontamination chamber 16. In some embodiments, the pressure in the decontamination chamber 16 is reduced to less than 10 torr. The system controller 20 may command the pressure controller 18 to develop the pressure differential before, during, or after the generation of the fog F in the chemical chamber 14. In some embodiments, a pressure gauge 30 is provided on the decontamination chamber 16 to allow a user to monitor the pressure inside of the decontamination chamber 16. The system controller 20 may also monitor the pressure inside of the decontamination chamber 16 automatically, such as based on a program stored in the system controller 20.

When the pressure inside of the decontamination chamber 16 reaches the desired or preprogrammed level, the system controller 20 opens the fluid control valve 24. Alternatively, the fluid control valve 24 may be manually actuated to an open state. This causes the fog F inside of the chemical chamber 14 to be transferred into the decontamination chamber 16 due to the difference in pressure between the two chambers. The fluid control valve 24 may be maintained in an open state until some or all of the fog F is transferred to the decontamination chamber 16, until a predetermined density of the fog F is reached in the decontamination chamber 16 and/or until the pressures between chambers 14 and 16 equalize. The amount of time that the fluid control valve 24 is maintained in an open state may be programmed into the system controller 20. As the fog F is transferred into the decontamination chamber 16, the pressure inside the decontamination chamber rises. In some embodiments, the pressure rises to a sub-atmospheric pressure when the fog F is transferred into the decontamination chamber 16. The fluid control valve 24 is then closed to prevent fluid flow between the chemical chamber 14 and the decontamination chamber 16. It should be noted that while the transfer of the fog F from the chemical chamber 14 to the decontamination chamber 16 has been described with regard to producing a vacuum inside of the decontamination chamber 16, other techniques may be used. For example, the fog F may be transferred into the decontamination chamber 16 employing a forced air assembly in the chemical chamber 14 to blow the fog F into the decontamination chamber 16.

In an alternative embodiment, the nozzle 22 is connected to the decontamination chamber 16 such that the fog F generated by the nozzle 22 is dispersed directly into the decontamination chamber 16. In this embodiment, the system 10 may not include the chemical chamber 14.

The fog F is held in the decontamination chamber 16 for an amount of time sufficient to decontaminate the medical device disposed therein. This amount of time may be programmed into the system controller 20, and may be based on the size and type of medical device being decontaminated. When the fog F has been held in the decontamination chamber 16 for the desired or programmed amount of time, the system controller 20 commands the pressure controller 18 to again evacuate the decontamination chamber 16 to reduce the pressure in the decontamination chamber 16 and remove the fog F from the decontamination chamber 16. This also causes the fog F to transition to its vapor phase in the decontamination chamber 16. In some embodiments, the pressure in the decontamination chamber 16 is reduced to less than 10 torr. In some embodiments, the decontamination chamber 16 is maintained at the reduced pressure for a programmed period of time.

The steps of developing the fog F, transferring the fog F into the decontamination chamber 16, and evacuating the decontamination chamber 16, may be performed a plurality of times. For example, after the fog F is evacuated from the decontamination chamber 16 in a first cycle as described above, a fog F in a second cycle may be introduced into the decontamination chamber 16. In one exemplary approach, the fog F for the second cycle is generated during the first cycle (e.g., while the decontamination chamber 16 is evacuated to remove the fog F) or after the first cycle. The pressure in the decontamination chamber 16 and state of the fluid control valve 24 may then be controlled as described above to introduce the fog F into the decontamination chamber 16. The fog F from the second cycle is then held in the decontamination chamber 16, and the decontamination chamber 16 is evacuated to removed the fog F as described above. While the system has been described with regard to first and second cycles, the system controller 20 may be programmed to repeat the decontamination cycle any number of times.

The system controller 20 may then command the decontamination chamber 16 to open an outlet 32 to vent the decontamination chamber 16 to atmospheric pressure. The decontamination chamber 16 may include an assembly to force the fog F through the outlet 32 to remove the fog F from the interior of the decontamination chamber 16. For example, the pressure controller 18 may be configured to draw the fog F through the outlet 32 or to push the fog F through the outlet 32. The outlet may include a filter that neutralizes and/or captures vapors of the fog F as it passes through the outlet 32. In some embodiments, the filter is a carbon based filter.

To assure complete removal of the decontaminating substance 26 from the decontamination chamber 16, the system controller 20 may then command the pressure controller 18 to again evacuate the decontamination chamber 16 to reduce the pressure within the decontamination chamber 16. In some embodiments, the pressure in the decontamination chamber 16 is reduced to less than 10 torr. The system controller 20 may then command the decontamination chamber 16 to open the outlet 32 to vent the decontamination chamber 16 to atmospheric pressure.

Figure 2:
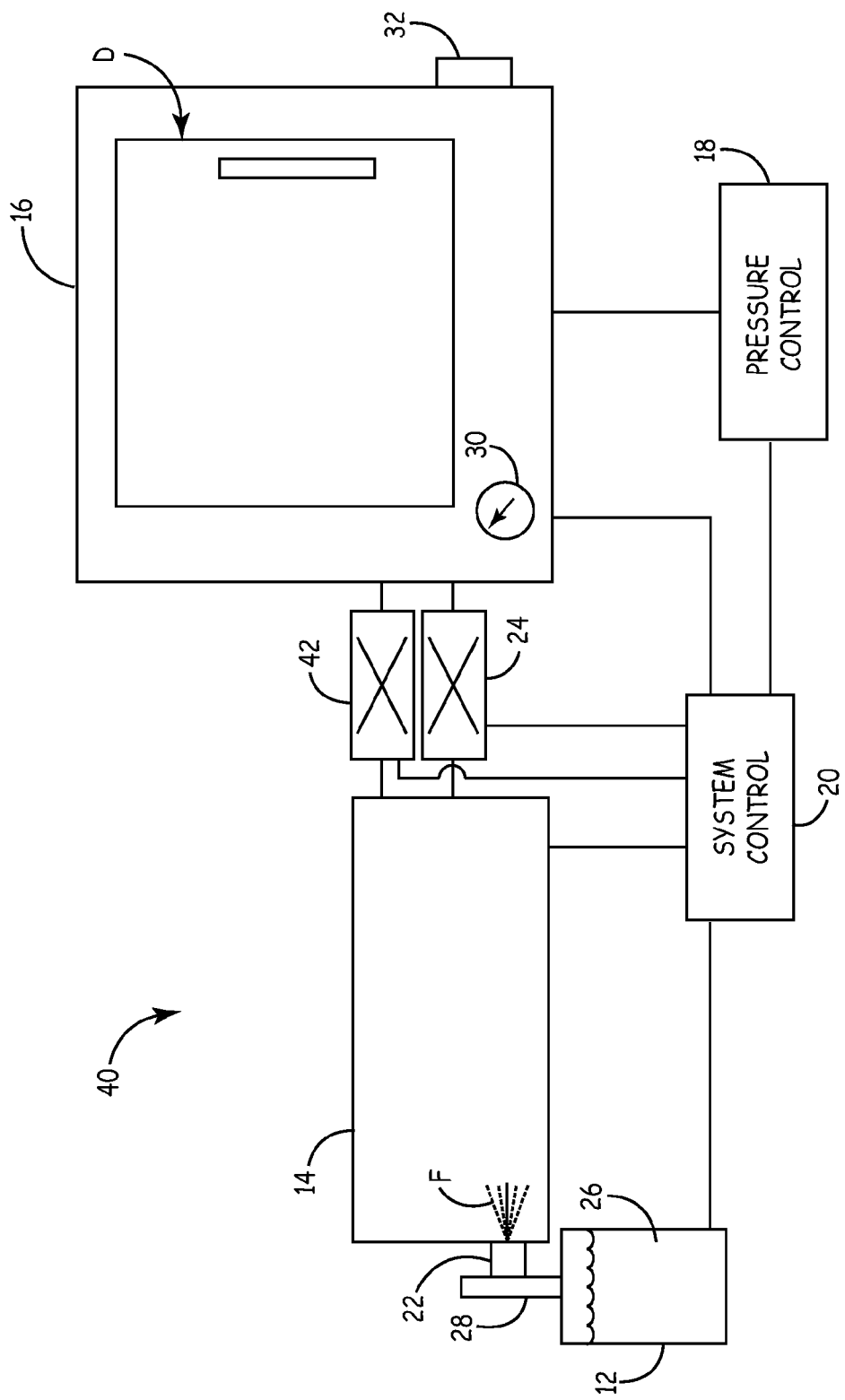
FIG. 2 is a schematic view of a system for decontaminating a medical device contained in a pouch or other enclosure, according to another embodiment of the present invention.

FIG. 2 is a schematic view of a system 40 for decontaminating a medical device according to another embodiment of the present invention. Similar to the system 10 of FIG. 1, the system 40 includes a reservoir 12, a chemical or fog chamber 14, a decontamination chamber 16, a pressure controller 18, a system controller 20, and a nozzle 22. These components of the system 40 may have substantially the same properties, configurations, and arrangements as described above with regard to system 10. In some embodiments, the system 40 is assembled in a device small enough to sit on a tabletop or counter, similar to system 10. In other embodiments, the components of system 40 may be separate and have any shape or size.

Some medical devices include tubes and other components having channels that can be difficult to access with the decontaminating substance during the decontamination process. For example, endoscopes, such as colonoscopes, gastroscopes, bronchoscopes, duodenoscopes, enteroscopes, and the like, may include a flexible or rigid tube including one or more channels that allow entry of medical instruments or manipulators. The system 40 is configured to provide the fog F to the interior of the medical device channel during the decontamination process. In particular, the system 40 includes a second fluid control valve 42 that provides a controllable fluid connection between the chemical chamber 14 and an interior of a medical device channel.

Similar to the system 10 discussed above, the system controller 20 commands the pressure controller 18 to develop a pressure differential between the chemical chamber 14 and the decontamination chamber 16 after the desired or programmed amount of fog F has been produced in the chemical chamber 14. For example, the pressure controller 18 may produce a vacuum or partial vacuum in the decontamination chamber 16. The system controller 20 then opens the fluid control valve 42 or, alternatively, the fluid control valve 42 is manually actuated to an open state. This causes the fog F inside of the chemical chamber 14 to be forced through the channel of the endoscope due to the difference in pressure between the two chambers. The fluid control valve 42 may be maintained in an open state until some or all of the fog F is transferred into the endoscope channel, until a predetermined density of the fog F is reached in the endoscope channel, and/or until the pressures between chambers 14 and 16 equalize. The amount of time that the fluid control valve 42 is maintained in an open state may be programmed into the system controller 20. The fluid control valve 42 is then closed to prevent fluid flow between the endoscope channel and the chemical chamber 14. It should be noted that while the transfer of the fog F from the chemical chamber 14 to the endoscope channel has been described with regard to producing a vacuum inside of the decontamination chamber 16, other techniques may be used. For example, the fog F may be forced into the endoscope channel employing a forced air assembly in the chemical chamber 14 to blow the fog F into the endoscope channel.

The system controller 20 then commands the reservoir 12 to generate additional fog F in the chemical chamber 14. When the desired or programmed amount of fog F has been dispersed into the chemical chamber 14, the fog F is transferred into the decontamination chamber 16. In some embodiments, the system controller 20 commands the pressure controller 18 evacuate the decontamination chamber 16 to develop a pressure differential between the chemical chamber 14 and the decontamination chamber 16. The system controller 20 may command the pressure controller 18 to develop the pressure differential before, during, or after the generation of the fog F in the chemical chamber 14. In some embodiments, the ambient conditions inside the decontamination chamber 16 are also controllable with system controller 20. For example, the temperature and/or humidity, which may affect the efficacy of the fog F, may be controlled by the system controller 20 to bring the decontamination chamber 16 to the desired conditions.

When the pressure and other conditions inside of the decontamination chamber 16 reaches the desired or preprogrammed level, the system controller 20 opens the fluid control valve 24, or the fluid control valve 24 is manually actuated to an open state. This causes the fog F inside of the chemical chamber 14 to be transferred into the decontamination chamber 16, thereby surrounding the exterior of the endoscope with the fog F. The fluid control valve 24 may be maintained in an open state until some or all of the fog F is transferred to the decontamination chamber 16, until a predetermined concentration of the fog F is reached in the decontamination chamber 16 and/or until the pressures between chambers 14 and 16 equalize. In some embodiments, the decontamination chamber 16 includes a chemical sensor in communication with the system controller 20 to measure the concentration of the fog F in the chamber 16. The amount of time that the fluid control valve 24 is maintained in an open state may be programmed into the system controller 20. The fluid control valve 24 is then closed to prevent fluid flow between the chemical chamber 14 and the decontamination chamber 16.

The fog F is held in the interior of the endoscope and the decontamination chamber 16 for an amount of time sufficient to decontaminate the endoscope. This amount of time may be programmed into the system controller 20, and may be based on the size and type of medical device being decontaminated.

When the fog F has been held in the decontamination chamber 16 for the desired or programmed amount of time, the system controller 20 commands the pressure controller 18 to again evacuate the decontamination chamber 16 to reduce the pressure inside the decontamination chamber 16 and remove the fog F from the decontamination chamber 16. This also causes the fog F to transition to its vapor phase in the decontamination chamber 16. In some embodiments, the pressure in the decontamination chamber 16 is reduced to less than 10 torr. In some embodiments, the decontamination chamber 16 is maintained at the reduced pressure for a programmed period of time.

Similar to the embodiment above, the steps of developing the fog F, transferring the fog F into the decontamination chamber 16 and/or medical device lumen and reducing the pressure in the decontamination chamber 16 may be performed a plurality of times. For example, after the fog F is evacuated from the decontamination chamber 16 in a first cycle as described above, a fog F in a second cycle may be introduced into the decontamination chamber 16 and/or medical device lumen, held, and subsequently evacuated in a process similar to the process described above.

The system controller 20 may then command the decontamination chamber 16 to open an outlet 32 to vent the decontamination chamber 16 to atmospheric pressure. The decontamination chamber 16 may include an assembly to force the fog F through the outlet 32 to remove the fog F from the interior of the endoscope and the decontamination chamber 16. For example, the pressure controller 18 may be configured to draw the fog F through the outlet 32 or to push the fog F through the outlet 32. The outlet may include a filter that neutralizes and/or captures vapors of the fog F as it passes through the outlet 32. In some embodiments, the filter is a carbon based filter.

To assure complete removal of the decontaminating substance 26 from the decontamination chamber 16 and endoscope, the system controller 20 may then command the pressure controller 18 to again reduce the pressure in the decontamination chamber 16 to produce a vacuum or partial vacuum within the decontamination chamber 16. In some embodiments, the pressure in the decontamination chamber 16 is reduced to less than 10 torr. The system controller 20 may then command the decontamination chamber 16 to open the outlet 32 to vent the decontamination chamber 16 to atmospheric pressure.

In some embodiments, the endoscope or other medical device to be decontaminated by the system 40 is contained in a pouch or other enclosure before, during, and after the decontamination process. The pouch is configured to facilitate connection between the fluid control valve 42 at an exterior of the pouch and one end of the endoscope channel at the interior of the pouch. After the decontamination process is completed, the endoscope or other device is retained in the pouch and remains decontaminated during storage and preferably beyond when the pouch is opened so the device can be used for a medical procedure.

Figure 3A:
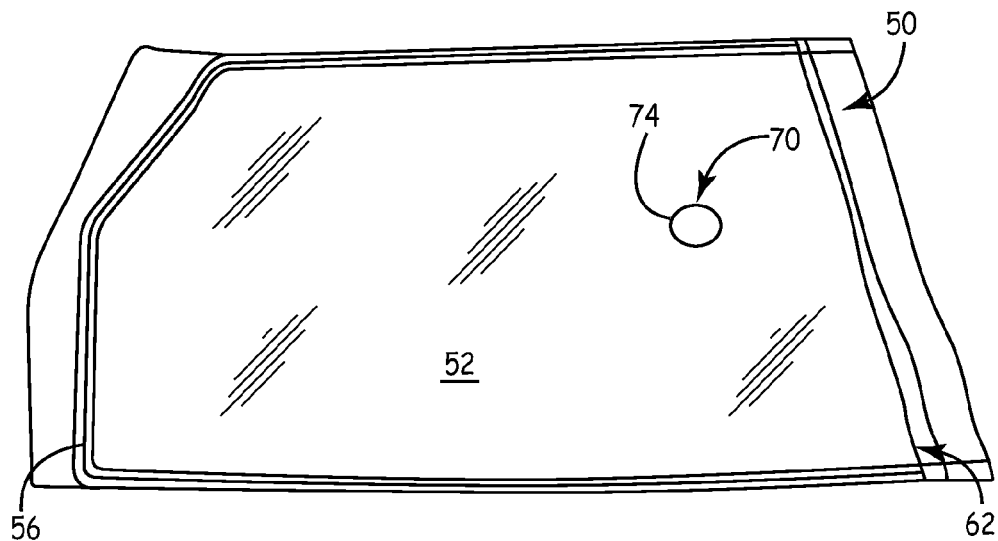
FIG. 3A is a front view of a pouch for retaining a medical device during and after decontamination in the system of FIG. 2.
Figure 3B:
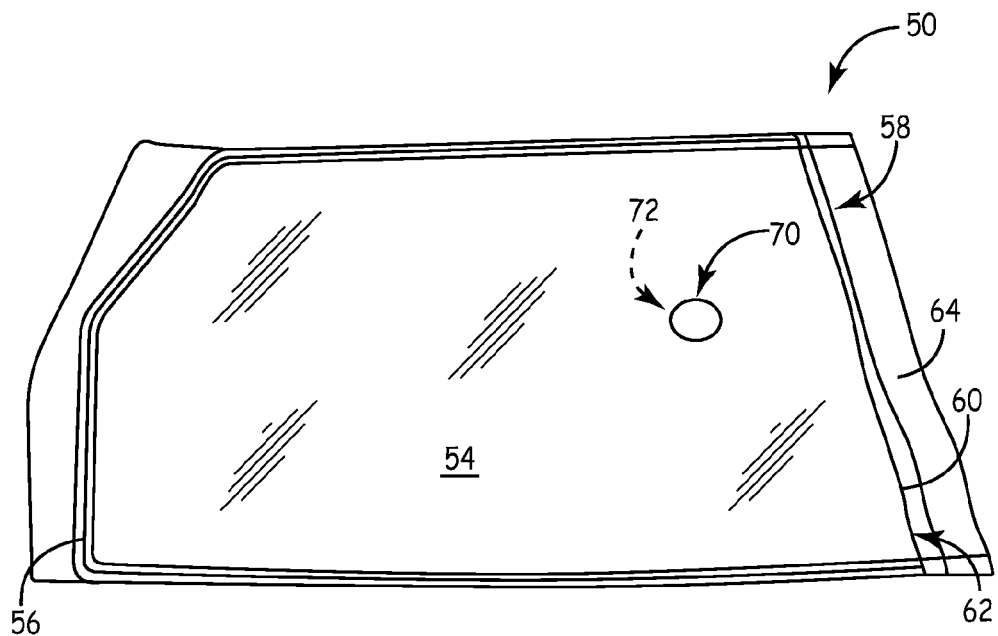
FIG. 3B is a rear view of a pouch for retaining a medical device during and after decontamination in the system of FIG. 2.

FIG. 3A is a front view and FIG. 3B is a rear view of an embodiment of a pouch 50 that is suitable for retaining a medical device before, during, and after decontamination of the medical device by the system 40. The pouch 50 can be constructed in a variety of ways including two discrete components that each form a side or one component that is folded over to provide both sides, either of which can be joined with heat seals, adhesives, or other seal types. The pouch 50 can be flat, gusseted, or otherwise constructed. For example, in the illustrated embodiment, the pouch 50 includes a front pouch layer 52 and a back pouch layer 54.

In some embodiments, the front pouch layer 52 comprises a polymeric non-woven sheet, such as spun-bonded polyethylene (e.g., Tyvek®, sold by E. I. du Pont de Nemours and Company, Wilmington, Del.). In other embodiments, the front pouch layer 52 comprises a polymeric material, such as polyester or polypropylene. In these embodiment, the polymeric material may include windows or sections of non-woven polymeric material. The back pouch layer 54 may comprise a transparent sheet of polymeric material, or may comprise an opaque or translucent layer of material. For example, the back pouch layer 54 may also comprise a polymeric non-woven sheet, or may comprise a polymeric material with windows or sections of non-woven polymeric material.

The pouch layers 52 and 54 may be bonded together by a perimeter seal 56 (such as by heat sealing) around three of the four sides of the pouch layers 52 and 54 to form the pouch 50 with an initially open end 58, formed by an open edge 60 of the front pouch layer 52 that is not bonded to the back pouch layer 54. The front pouch layer 52 may be perforated along a fold line 62 and may include a strip of contact adhesive 64 along the open edge 60. The perforation is outside of the seal area and does not break the decontamination barrier of the pouch 50. The contact adhesive may initially include a release layer that covers the strip of contact adhesive 64. To facilitate connection of the endoscope or other medical device to the fluid control valve 42, the pouch 50 includes an integrated connection port 70. In the embodiment shown, the connection port 70 is coupled to the front pouch side 52. The connection port 70 may be secured to the front pouch side 52 by, for example, bonding the connection portion 70 to the front pouch side. While a single connection port 70 is shown, multiple connection ports 70 may be secured to the pouch 50 to allow multiple internal interfaces of medical devices to be connected to the pouch 50.

Figure 4:
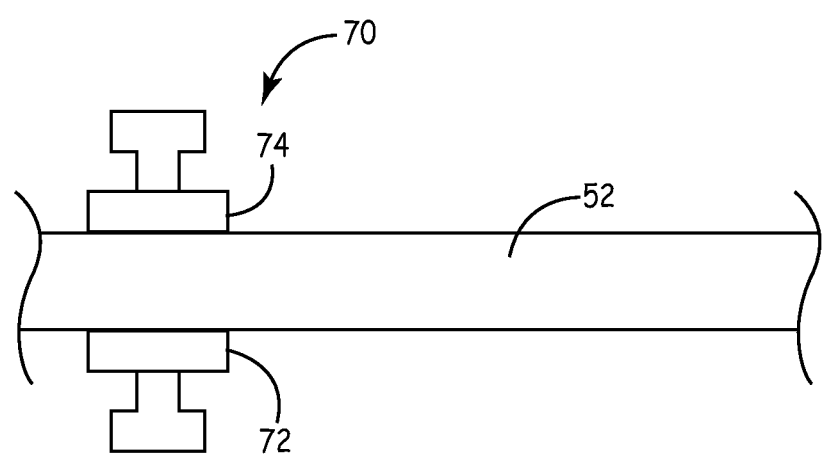
FIG. 4 is a cross-sectional view of a connector on the pouch of FIGS. 3A and 3B suitable for interfacing with the system of FIG. 2.

FIG. 4 is a cross-sectional view of an embodiment of the connection port 70 coupled to the front pouch layer 52 (not to scale). The connection port 70 includes an internal interface 72 and an external interface 74. The internal interface 72 is configured to couple with a mating interface on the endoscope, and the external interface 74 is configured to couple with a mating interface on the fluid control valve 42. In some embodiments, the internal interface 72 and/or the external interface 74 each includes a Luer lock fitting or other suitable connector. In some embodiments, the internal interface 72 and/or the external interface 74 is/are comprised of a polymeric material that is adhesively attached to the front pouch layer 52. In other embodiments, the internal interface 72 and/or the external interface 74 is/are comprised of polyethylene and is heat-affixed to the front pouch layer 52.

In the embodiment shown, the internal interface 72 and the external interface 74 are aligned with each other across the front pouch layer 52. The external interface 74 may be a one way valve that seals when the external interface is disconnected from the fluid control valve 42. In other embodiments, the internal interface 72 and external interface 74 are coupled to each other through an aperture in the front pouch layer 52 and sealed to the front pouch layer 52 around a periphery of the interfaces 72, 74. In one alternative embodiment, the connection port 70 includes only an internal interface 72 that abuts the inner pouch layer and is configured to couple with an endoscope. In another alternative embodiment, the connection port 70 includes only an external interface 74 that couples with the system 40.

In use, the endoscope is placed into the pouch 50, and a channel opening of the endoscope is mechanically coupled to the internal interface 72. The mechanical coupling is sufficient to hold together the pouch 50 and interface 72 during the decontamination process, which can impose a force that would otherwise separate the pouch 50 and interface 72. In some embodiments, a manifold including a plurality of fluid paths is connected to the internal interface 72 to allow for connection of the system to a plurality of channels in the endoscope. In alternative embodiments, the pouch 50 includes a plurality of connection ports 70 that are each connectable to an endoscope channel. For endoscopes that do not include interior channels, the endoscope is placed into the pouch 50 without connection to the internal interface 72. In other alternative embodiments, the connection port 70 on the pouch 50 may be configured to include an external interface 74 with no internal interface 72.

The pouch 50 is then sealed by folding the front pouch layer 52 along the fold line 62 and sealing the front pouch layer 52 to the back pouch layer 54 via the contact adhesive 64. The external interface 74 is then coupled to the fluid control valve 42. For example, the interior of the decontamination chamber 16 may include an integrated assembly that facilitates fluid coupling between the external interface 74 and the fluid control valve 42. In some embodiments, a plurality of pouches 50 each with an endoscope or other medical device therein is placed in the decontamination chamber 16 and coupled to a fluid control valve. After the door D to the decontamination chamber 16 is closed, the decontamination process can begin.

After the desired or programmed amount of fog F is produced in the chemical chamber 14, and the pressure controller 18 develops a pressure differential between the chemical chamber 14 and the decontamination chamber 16, the fluid control valve 42 is automatically or manually opened. This forces the fog F into the interior of the endoscope channel. As discussed above, the fog F may alternatively be introduced directly into the decontamination chamber 16, such that the fog F is provided directly to the interior of the decontamination chamber 16 and/or the interior of the endoscope channel.

As discussed above, the front pouch layer 52 may be comprised of a non-woven sheet of material, which includes open spaces between fibers of the material or pores sufficiently large to allow passage of the small vapor particles of the fog F. Thus, in the embodiment of the connection port 70 shown in FIG. 4, the fog F passes through the external interface 74, the front pouch layer 52, the internal interface 72, before entering the endoscope channel. In embodiments in which the internal interface 72 is coupled to the external interface 74 via an aperture in the front pouch layer 52, the fog F passes through the external interface 74 and the internal interface 72 before entering the endoscope channel. In embodiments including only an internal interface 72, the fog F may be forced through the front pouch layer 52 and into the endoscope channel via the internal interface 72. In embodiments including only an external interface 74, the fog F may be forced through the front pouch layer 52 and into the interior of the pouch 50. In each embodiment, the fog F may be held in the interior of the pouch 50 and, in certain cases, the endoscope channel for a predetermined time.

After the fluid control valve 42 is closed, fog F is produced in the chemical chamber 14, and the pressure controller 18 develops a pressure differential between the chemical chamber 14 and the decontamination chamber 16. In some embodiments, the fluid control valve 24 is then optionally opened to force the fog F into the interior of the decontamination chamber and around the exterior of the pouch 50. The fluid control valve 24 is then closed.

When the fog F has been held in the decontamination chamber 16 for the desired or programmed amount of time, the pressure in the decontamination chamber 16 is reduced as described above. The fog F may be introduced into the pouch 50 and decontamination chamber 16, held, and the pressure subsequently reduced a plurality of times. The system controller 20 then commands the decontamination chamber 16 to open the outlet 32 and force the fog F through the open outlet 32 and remove substantially all fog F from the interior of the decontamination chamber 16. As discussed above, the pressure controller 18 may be configured to draw the fog F through the outlet 32 or to push the fog F through the outlet 32. During this process, the fog F in the endoscope channel and the interior of the pouch 50 is drawn through the front pouch layer 52, into the interior of the decontamination chamber 16, and out through the outlet 32. To assure complete removal of the fog F from the pouch 50, endoscope channel, and decontamination chamber 16, the pressure may be reduced, and subsequently vented to atmospheric pressure one or more additional times.

After the fog F has been removed from the decontamination chamber 16, the endoscope channel, and the interior of the pouch 50, the decontamination process may be repeated for a desired or preprogrammed number of cycles. When all cycles have been completed, the pouch 50 containing the endoscope sealed therein may be removed from the decontamination chamber 16. In some embodiments, the pouch 50 includes a marker or indicator that shows that the pouch 50 has been through one or more decontamination cycles in the system 40. In some embodiments, the indicator is a biological indicator or chemical indicator. For example, the pouch 50 may include a material that changes color when exposed to the decontamination substance. In embodiments of the pouch 50 including an aperture through pouch layers 52 or 54 to provide a path for the fog F, the aperture may be heat sealed before or after the pouch 50 is removed from the decontamination chamber 16.

When the process is completed, the endoscope remains decontaminated until the pouch 50 is opened for a procedure. That is, the endoscope remains in a terminally decontaminated state after the pouch 50 is disconnected and removed from the decontamination system. For example, in embodiments in which the front pouch side 52 is comprised of a polymeric non-woven sheet, the structure of the front pouch side 52 prevents ingress of contaminants into the interior of the pouch 50.

Figure 5A:
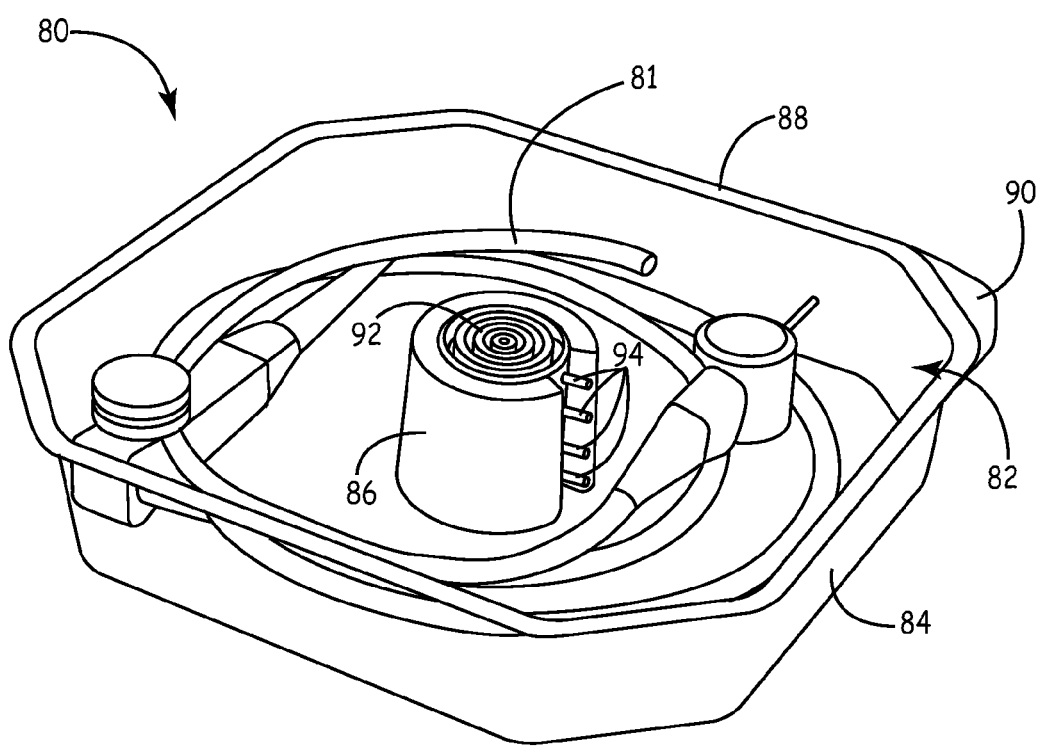
FIG. 5A is a perspective view of a package for retaining a medical device during and after decontamination in the system of FIG. 2.

FIG. 5A is a perspective view of an embodiment of a package 80 that is also suitable for retaining a medical device 81 before, during, and after decontamination of the medical device by the system 40. The package 80 includes a front cover layer 82, a container 84, and a connector support 86. In some embodiments, the front cover layer 82 comprises a polymeric non-woven sheet, such as spun-bonded polyethylene-based non-woven material (e.g., Tyvek®, sold by E. I. du Pont de Nemours and Company, Wilmington, Del.). In other embodiments, the front cover layer 82 comprises a polymeric material, such as polyester or polypropylene. The container 84 may be comprised a transparent, translucent, or opaque resilient polymeric material.

The front cover layer 82 and the container 84 may be bonded together by a perimeter seal 88 (such as by heat sealing) to retain the medical device 81 within the package 80. The front cover layer 82 may extend beyond the perimeter of the package 80 on at least one corner to produce a tab 90 that facilitates disengagement of the front cover layer 82 from the container 84 to access the sterilized medical device 81.

Figure 5B:
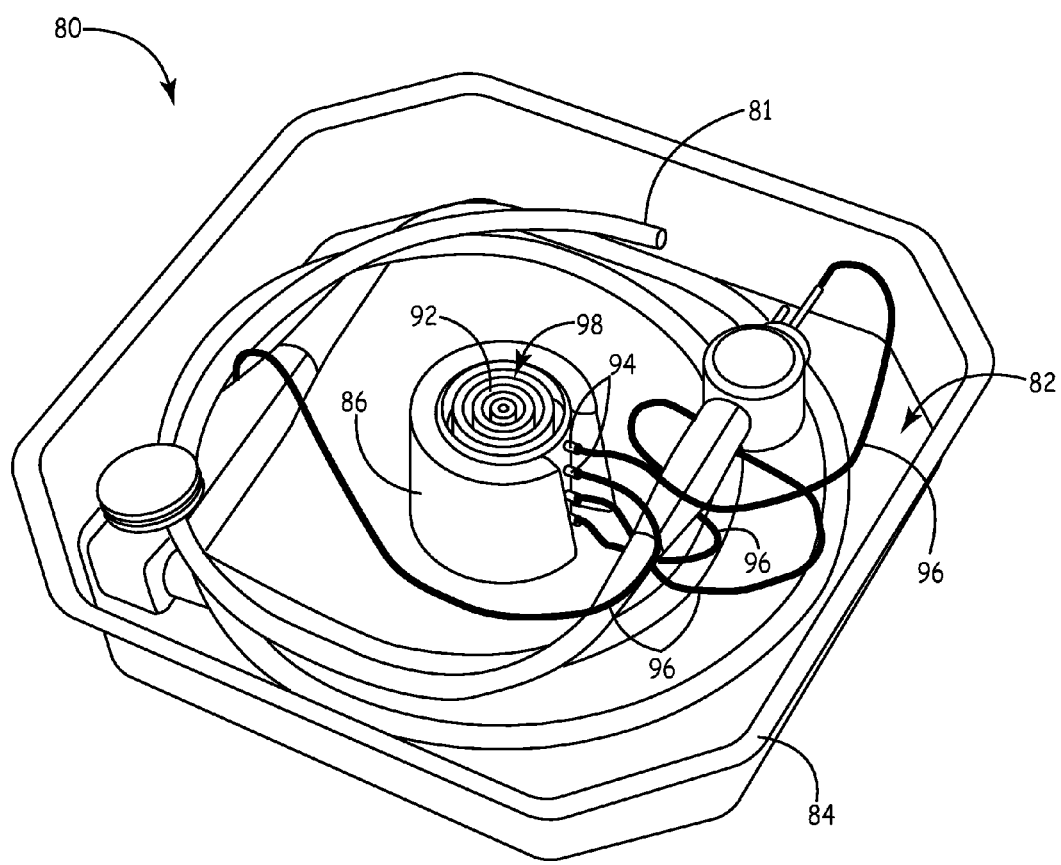
FIG. 5B is a perspective view of the package of FIG. 5A with the cover removed and illustrating a connector that couples to the medical device.

To facilitate connection of the endoscope or other medical device to the fluid control valve 42, the connector support 86 is configured to retain a connector 92 that includes one or more connection interfaces 94 that may be coupled to channels or ports on the medical device 81. FIG. 5B is a perspective view of the package 80 with the front cover layer 82 removed to illustrate coupling of the connection interfaces 94 to the medical device. A conduit 96 is connected to each of the connection interfaces 94 on the connector 92 at one end and to the medical device 81 at the other end. For example, the medical device 81 may be an endoscope, and the conduits 96 may be coupled to channels in the endoscope to provide a fluid path from between the connector 92 and the channels. The connector 92 includes openings 98 that connect the connection interfaces 94 to the top of the connector 92. In cases in which the medical device 81 does not include interior channels, the medical device 81 may be placed in the container 84 without coupling to the connector 92.

When the medical device 81 has been coupled to the connector 92 as desired, the package 80 may then be sealed by securing the front cover layer 82 to the container 84 as shown in FIG. 5A. The front cover layer 82 may be sealed onto the container 84 prior to putting the package 80 into the decontamination chamber 16. Alternatively, the decontamination chamber 16 may be configured to mount the front cover layer 82 to the container 84 before, during, or after the decontamination process. The decontamination chamber 16 may include an interface that couples with the connector 92 through the front cover layer 82 to connect the connector 92 to the fluid control valve 42. In some embodiments, a plurality of packages 80 each with an endoscope or other medical device therein is placed in the decontamination chamber 16 and coupled to a fluid control valve. After the door D to the decontamination chamber 16 is closed, the decontamination process can begin.

The decontamination process for the medical device 81 in the package 80 may be substantially similar to the decontamination process described above with regard to the pouch 50. When all decontamination cycles have been completed, the package 80 containing the endoscope sealed therein may be removed from the decontamination chamber 16. In some embodiments, the package 80 includes a marker or indicator that shows that the package 80 has been through one or more decontamination cycles in the system 40. For example, the package 80 may include a material that changes color when exposed to the decontamination substance. When the process is completed, the endoscope remains decontaminated until the package 80 is opened for a procedure. In some embodiments, after the package 80 is opened and the endoscope or other medical device is removed from the package 80, the connector 92 may be removed from connector support 86 for subsequent use in another package 80.

EXAMPLE

Three endoscopes, Endoscope A, Endoscope B, and Endoscope C, were tested in the system 40. Endoscope A was a single channel, single connection endoscope with a biopsy channel having a diameter of 2 mm and a length of 610 mm. Endoscope B was a multichannel, multi-connection endoscope with an air channel having a diameter of 1 mm and a length of 4,013 mm, a water channel having a diameter of 2 mm and a length of 4,013 mm, and a suction/biopsy channel having a diameter of 4 mm, and a length of 4,013 mm. Endoscope C was a single channel, two-connection endoscope with a biopsy channel having a diameter of 2.2 mm and a length of 550 mm.

The three endoscopes were inoculated to a total inoculum concentration of approximately $10^6$ colony-forming units (CFU). The test organism used in Endoscope A was *bacillus subtilis*, and the test organism used in Endoscopes B and C was *bacillus atrophaeus*. The three endoscopes were then each placed in a pouch 50 and connected internal interface 72 of the port 70. For each endoscope, the pouch 50 was then sealed and placed in the decontamination chamber 16, and second fluid control valve 42 was connected to the external interface 74 of the port 70.

The three endoscopes were then subjected to a decontamination cycle wherein the fog F was introduced into the channel(s) of the endoscope by reducing the pressure in the decontamination chamber 16 to about 400 Torr, and the pressure was held at about 400 Torr for a period of time. The pressure in the decontamination chamber 16 was then increased to about 700 Torr to draw the fog F through the front pouch layer 52 and into the decontamination chamber 16. The pressure in the decontamination chamber 16 was then reduced again to about 400 Torr, increased to about 700 Torr, reduced again to about 400 Torr, and subsequently vented to atmospheric pressure to draw remaining fog F out of the pouch 50 and the decontamination chamber 16.

The endoscopes were then analyzed with a surviving organism recovery method. In four tests, Endoscope A experienced a log reduction of *bacillus subtilis* of between about 6.26 and about 7.24. In five tests, Endoscope B experienced a log reduction of *bacillus atrophaeus* of between about 4.66 and about 6.9. In one test, Endoscope C experienced a log reduction of *bacillus atrophaeus* of greater than 6.83.

In summary, the present invention relates to an enclosure for retaining an endoscope or other devices during and after a decontamination process. In some embodiments, the enclosure is a pouch including a first pouch side, a second pouch side attached to the first pouch side to form the pouch that is configured to retain the endoscope, and a port member coupled to the second pouch side. The second pouch side is securable to the first pouch side to seal the endoscope within the pouch. The second pouch side is configured to permit passage of a decontaminating substance. The port member is coupled to the second pouch side and includes an external interface configured to be connected to a device that provides the decontaminating substance for passage through the port member into an interior of the pouch. In other embodiments, the enclosure is a package including a container that retains the endoscope and a cover layer that seals the medical device in the container during and after the decontamination process. The endoscope is intended to remain in the package after decontaminating and remains decontaminated after the package is opened. In some embodiments, the decontaminating substance is approximately room temperature and is provided to the pouch as a fog. In other aspects, the present invention relates to a system for decontaminating a medical device with a approximately room temperature fog.

Various modifications and additions can be made to the exemplary embodiments discussed, and various other combinations of aspects or features of such embodiments can be made, without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof, such as other pouch and valve configurations.

We claim:

1. A method for decontaminating a medical device, the method comprising:
    enclosing the medical device in an enclosure, the enclosure including a fog-permeable layer and an exterior port member and an interior port member coupled to the fog-permeable layer;
    placing the enclosure within a decontamination chamber;
    coupling the exterior port member of the enclosure to a chemical dispersing interface in the decontamination chamber;
    reducing a pressure in the decontamination chamber to a sub-atmospheric pressure in a first evacuation step;
    introducing a room temperature decontaminating fluid as a fog into the enclosure within the decontamination chamber by flowing the fog through the exterior port member, the fog-permeable layer, the interior port member, and at least a portion of the medical device;
    holding the fog in the enclosure and the decontamination chamber for a decontaminating time;
    reducing the pressure in the decontamination chamber to a sub-atmospheric pressure in a second evacuation step; and
    venting the decontamination chamber to atmospheric pressure.

2. The method of claim 1, wherein the introducing step comprises forcing the decontaminating fluid through an atomizing nozzle to transform the decontaminating fluid into the fog.

3. The method of claim 1, wherein the introducing step comprises:
    dispersing the fog into a chemical chamber;
    developing a pressure differential between the decontamination chamber and the chemical chamber; and
    opening a pressure control valve between the decontamination chamber and the chemical chamber.

4. The method of claim 1, wherein the enclosure is a pouch and wherein the enclosing step comprises placing the medical device in the pouch including a first pouch side, a second pouch side attached to the first pouch side to form the pouch that is configured to retain the medical device, and a port member coupled to the second pouch side, the second pouch side further securable to the first pouch side to seal the medical device within the pouch, wherein the second pouch side has an interior surface and an exterior surface, and wherein the second pouch side is fog-permeable, the port member including the exterior port member which is configured to be connected to the chemical chamber.

5. The method of claim 4, wherein the port member further includes an interior port member configured to be connected to the medical device, and wherein the introducing step comprises forcing the fog through the exterior port member, second pouch side, interior port member, and at least a portion of the medical device.

6. The method of claim 1, and further comprising holding the decontamination chamber at the reduced pressure for a period of time after the second reducing step.

7. The method of claim 1, wherein after the venting step, the method further comprises:
    reducing the pressure in the decontamination chamber to a sub-atmospheric pressure in a third evacuation step; and
    venting the decontamination chamber to atmospheric pressure.

8. The method of claim 1, wherein the enclosure comprises
    a pouch having an internal side and an external side and comprising
        a first material layer defining an area and
        a second material layer defining an area, the first material layer and second material layer secured along a periphery of the first material layer area and the second material layer area;
    an interior port member coupled to the first material layer on the internal side of the pouch; and
    an external port member coupled to the first material layer on the external side of the pouch and in fluid communication with the interior port member,
    wherein a portion of the first material layer area is located between the interior port member and the external port member.

9. The method of claim 8, wherein the first material layer comprises a fog-permeable layer and wherein the introducing step includes flowing the decontaminating fluid through the external port member, through the portion of the first material layer located between the interior port and the external port member, through the internal port member, and into the enclosure within the decontamination chamber.

10. The method of claim 1, further comprising removing the enclosure from the decontamination chamber and wherein the medical device is retained in the enclosure in a terminally decontaminated state after the enclosure is removed from the decontamination chamber.

* * * * *